United States Patent [19]

Noe

[11] Patent Number: 4,712,546

[45] Date of Patent: Dec. 15, 1987

[54] CUTTING INSTRUMENT FOR NASAL SURGERY WHICH CUTS PARALLEL TO ITS LENGTH

[76] Inventor: Joel M. Noe, 59 Baxter Rd., Brookline, Mass. 02146

[21] Appl. No.: 357,265

[22] Filed: Mar. 11, 1982

[51] Int. Cl.[4] ............................................. A61F 17/32
[52] U.S. Cl. ..................................... 128/305; 433/144
[58] Field of Search ................. 433/143, 144; 30/287, 30/294; 128/305, 305.1, 751

[56] References Cited

U.S. PATENT DOCUMENTS

| | | | |
|---|---|---|---|
| 2,569,844 | 10/1951 | Berliner | 433/144 |
| 2,743,519 | 5/1956 | Hazelton | 30/294 |
| 3,241,236 | 3/1966 | Capps | 30/294 |
| 3,325,900 | 6/1967 | Sohlberg | 433/144 |

FOREIGN PATENT DOCUMENTS

| | | | |
|---|---|---|---|
| 172451 | 6/1963 | U.S.S.R. | 128/305 |
| 200727 | 10/1967 | U.S.S.R. | 128/305 |

OTHER PUBLICATIONS

Aesculap Main Catalog–Joseph OL 107.

Primary Examiner—C. Fred Rosenbaum
Assistant Examiner—J. L. Kruter
Attorney, Agent, or Firm—Robert L. Goldberg

[57] ABSTRACT

A cutting instrument for nasal surgery has an elongated portion, such as a handle, extending along a first direction and a first end which is intended to be pointed into a nostril during nasal surgery. A cutting extension extends from the elongated portion at approximately ninety degrees from the first direction. The cutting extension has first and second cutting edges which point in opposite directions parallel to the first direction and which extend in the second direction. In a preferred embodiment the cutting extension is placed approximately at the first end of the elongated portion and it has a non-cutting end which extends beyond the first and second cutting edges away from the elongated portion in the second direction.

5 Claims, 3 Drawing Figures

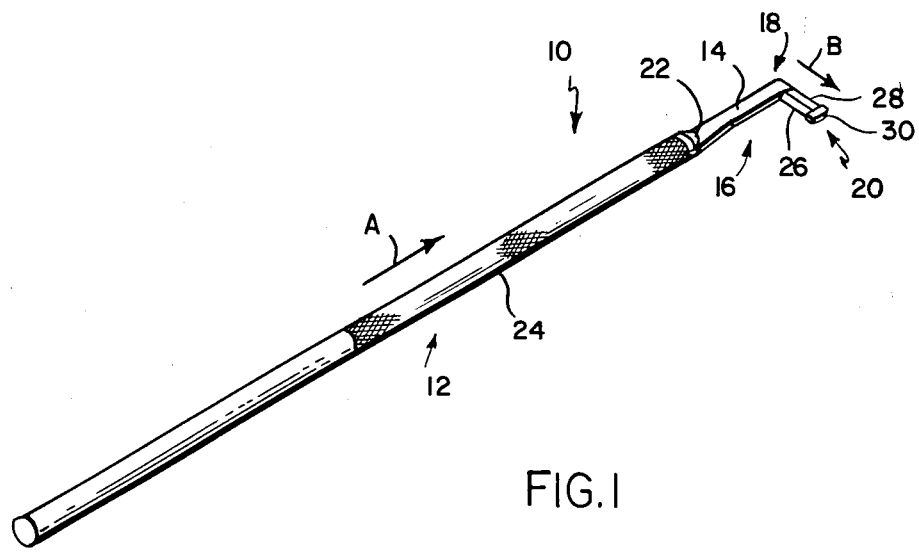
FIG. 1
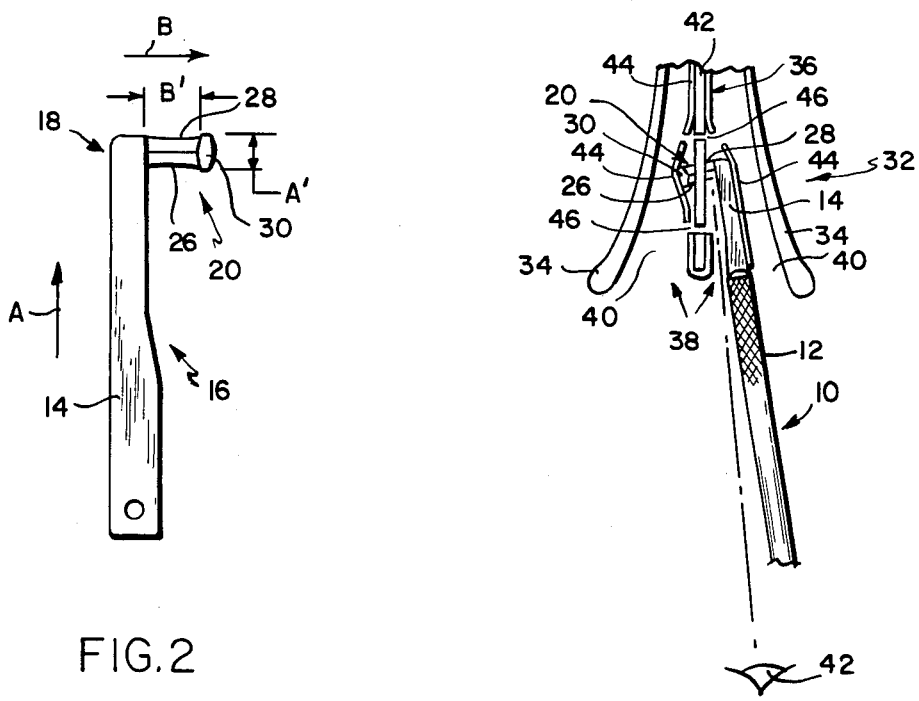
FIG. 2
FIG. 3

CUTTING INSTRUMENT FOR NASAL SURGERY WHICH CUTS PARALLEL TO ITS LENGTH

BACKGROUND OF THE INVENTION

1. Field of the Invention

The present invention relates generally to cutting instruments for nasal surgery and in particular to an instrument for cutting septal cartilage in operations such as submucous resections and rhinoplasty.

2. Description of the Prior Art

It is often desirable to perform an operation which involves cutting the nasal septum, that is, the septal cartilage which separates the two passages of the nose. For example, when a person with a broken nose has a deviated septum that blocks breathing in one of his nasal passages, a submucous resection is commonly performed in which a portion of the septal cartilage blocking his breathing is cut out. The septal cartilage is also cut in rhinoplasty, that is, cosmetic surgery performed to remove a hump from the nose.

One of the major difficulties in performing operations on the septal cartilage is the limited access which the nostrils and the nasal passages provide to the nasal septum. The nostrils are relatively small openings and the nasal passages are narros compared to their depth. The cutting instruments which have been used in the prior art for nasal surgery usually involve a relatively straight handle which holds a cutting edge that extends in the direction of the handle or at a relatively slight angle to it. Because of the orientation of the cutting surfaces on such instruments, it is difficult for them to enter a nasal passage and made a cut across the width of the nasal cartilage, without temporarily deforming the nostrils and the nose, particularly in portions of the cartilage far removed from the nostrils. In addition, the orientation of the cutting surfaces in such instruments often makes such cutting surfaces hard to see when they are cutting in the nose, because such cutting surfaces tend to be obscured by the handles to which they are attached.

The difficulties associated with such blades have caused the rather primative swivel knife to be commonly used in submucous resections. The swivel knife has a blade extended between two prongs attached to its handle. The blade swivels so that the angle in which it cuts can rotate about its axis between the two prongs. In a submucous resection using the swivel knife, the lower end of the nasal septum is separated from the columnella, the flesh separating the two nostrils. The mucous membranes on both sides of the septum are separated from the septum, and the collumnella is bent to one side to expose the lower end of the septum. The blade of the swivel knife is placed against the exposed end of the septum with the mucous membranes placed outside the knife's two prongs. Then the blade is moved in a generally circular motion to cut out a section of the septal cartilage. The swivel knife is a primative tool because it is difficult to accurately control its cutting motion, and its two prongs make it difficult to see what it is cutting.

OBJECTS OF THE INVENTION

Accordingly, it is an object of this invention to provide a cutting instrument for nasal surgery that avoids the abovementioned difficulties encountered with the prior art.

It is another object of the invention to provide a cutting instrument for nasal surgery which allows cutting of the septal cartilage without excessive bending of the nose.

It is a further object of the invention to provide a cutting instrument for nasal surgery which makes it easy to cut in a direction generally parallel to the longitudinal axis of that cutting instrument.

The above and other objects, features and advantages of the present invention will become readily apparent from the ensuing detailed description, and the novel features of the invention will be particularly pointed out in the appended claims.

SUMMARY OF THE INVENTION

In accordance with one aspect of this invention, a cutting instrument for nasal surgery is provided which comprises an elonganted portion extending along a first direction and having a first end which is intended to be pointed into a nostril during nasal surgery. A cutting extension extends from the elongated portion at approximately ninety degrees from the first direction. The cutting extension has first and second cutting edges which point in opposite directions parallel to the first direction and which extend in the second direction. In a preferred embodiment the cutting extension is placed approximately at the first end of the elongated portion and it has a non-cutting end which extends beyond the first and second cutting edges away from the elongated portion in the second direction.

BRIEF DESCRIPTION OF THE DRAWINGS

The following detailed description, given by way of example, would best be understood in conjunction with the accompanying drawings, in which:

FIG. 1 is a perspective view of a cutting instrument for nasal surgery according to the present invention;

FIG. 2 is a plan view of the surgical blade shown in FIG. 1 removed from its handle;

FIG. 3 is a schematic cross section of a human nose being cut by the cutting instrument shown in FIG. 1.

DETAILED DESCRIPTION OF A PREFERRED EMBODIMENT

Referring now to the drawings, a cutting instrument 10 for nasal surgery is shown which embodies the present invention. The cutting instrument 10 is comprised of an elongated portion comprised of a handle 12 and the stem 14 of a blade 16, which blade is removeably inserted into the front end of handle 12. The elongated portion formed by handle 12 and stem 14 extends in a first direction indicated by the arrow A and has a first end 18 which is intended to be pointed into a nostril during nasal surgery, as shown below in FIG. 3. At its end 18, blade 16 has a cutting extension 20, which extends from stem 14 in a second direction, indicated by arrow B, approximately 90° from direction A in which handle 12 and stem 14 extend.

Handle 12 is a surgical chuck handle, of a type well known in the surgical arts. It has a slotted receptical 22 for receiving the stem of a surgical blade, such a blade 16, which can be screwed into the remainder of handle 12 to tighten the slot of receptical 22 about the stem of the blade so as to firmly grip it. Handle 12 also contains a knurled portion 24 near its front so as to enable it to be firmly and precisely held.

FIG. 2 shows blade 16 removed from handle 12. Blade 16 is made from a relatively flat piece of stainless steel, which is shaped into stem 14 and cutting extension 20. Cutting extention 20 has two cutting edges, a first cutting edge 26 and a second cutting edge 28, which point in opposite directions parallel to direction A and which extend in the direction B, approximately perpendicular to direction A. Cutting extension 20 also has a non-cutting end 30 which extends beyond cutting edges 26 and 28 in direction B away from the elongated portion of cutting instrument 10 formed by stem 14 and, when it is attached to stem 14, handle 12.

In the preferred embodiment of the invention shown in the drawings, stem 14 is approximately thirty-three millimeters long. Cutting extension 20 is approximately eight millimeters long. And first and second cutting edges 26 and 28 are each approximately four millimeters long from their start near the stem 14 to their end at non-cutting end 30, the distance indicated as B' in FIG. 2. Although it is possible to vary the length of cutting edges 26 and 28 in alternative embodiments of the cutting instrument, it is best to have such cutting edges at least two millimeters in length, since the human septal cartilage is commonly between one and a half to two millimeters in width. In fact it is desirable to have the cutting edges at least four millimeters long, as in the preferred embodiment, because a septal cartilages which has been deformed by injury can reach thicknesses of almost four millimeters. However, if the cutting edges are two long, for example, if they are in excess of six millimeters in length, the cutting extension will become so long that its ability to be easily be fitted into and moved within a nostril will be reduced.

The width of cutting extension 20 in direction A, indicated a A' in FIG. 2, is approximately two and one-half millimeters. In alternative embodiments of the invention, it is desirable to keep such width of cutting extension 20 to less than three and one-half millimeters. In fact it is desirable to keep such width as small as is possible without sacrificing necessary strength and cutting characteristics. Such a small width of cutting extension 20 is desirable so that cutting extension can be turned with relative ease when it is cutting cartilage and so that it can be inserted with relative ease into a slit in the septum which extends in a direction perpendicular to that in which it cuts.

FIG. 3 is a simplified cross-sectional view of a human nose 32 which has been made to illustrate the operation of cutting instrument 10. Side walls 34 and nasal septum 36 of the nose define nostrils 38 and nasal passages 40. Septum 36 is comprised of the septal cartilage 42, which is covered on both sides by mucous membranes 44.

Before instrument 10 is inserted in the nose, septum 36 is cut by another instrument at locations 46 in a direction perpendicular to the paper of FIG. 3. An instrument particularly suited for making such perpendicular cuts is disclosed in patent application Ser. No. 357,266, filed Mar. 11, 1982 entitled "Cutting Instrument for Nasal Surgery Which cuts Perpendicular to its Length" filed by the inventor of the present invention on the same date as this application. Once the cuts at locations 46 have been made, the mucous membranes 44 are separated from both sides of the septal cartilage 42 by techniques well known in the art of nasal surgery. Then the end 18 of cutting instrument 10 is placed through a nostril 38, into a nasal passage 40, and between a portion of a mucous membrane 44 and the cartilage 42 from which it has been separated. At this point the elongated portion of instrument 10 is approximately parallel to septal cartilage 42 and cutting extension 20 extends approximately perpendicular to that cartilage. Non-cutting end 30 of cutting extension 20 is then pushed through one of the cuts at locations 46 so that the cutting edges 26 and 28 are in a position to cut septal cartilage 42 by either pushing or pulling handle 12 in a direction parallel to that handle's length. Non-cutting end 30 pushes the mucous membrane 44 on the far side of cartilage 42 out of the path of the cutting edges 26 and 28 and thus prevents that membrane from being cut. Similarly, the mucous membrane 44 on the same side of the cartilage as stem 14 is kept out of the way of cutting edges 26 and 28 by the non-cutting back of stem 14. Thus it is possible for instrument 10 to cut cartilage 42 without cutting its adjoining mucous membranes 44, as is often desired in nasal operations such a submucous resections.

As indicated by FIG. 3, the shape of cutting instrument 10 makes it possible to cut the septal cartilage without significantly bending nostrils 38 or side walls 34 of nose 32. In addition, the location of cutting edges 26 and 28 on cutting extension 20 causes those cutting surfaces to be less obscured by handle 12 and more visible from the eye 42 of a surgen looking up into nostril 38 than they would be if they did not stick out at such a sharp angle from stem 14. This is important, since it is very desirable in nasal surgery to see a blade as it cuts.

It can be seen by one skilled in the art that a cutting instrument according to the present invention could be made in which a handle different than handle 12 was used. For example, it should be obvious that the blade of the present invention could be used with other types of blade handles commonly used in the surgical arts, or that the cutting instrument of the present invention could be made with a handle that was permanently attached to a cutting extension such as cutting extension 20 shown in the drawings. Similarly it can also be seen that a blade, such as blade 16, which has an elongated portion and a cutting extension is by itself an embodiment of the present invention.

Having described a specific preferred embodiment of the invention with reference to the accompanying drawings, it is to be understood that the invention is not limited to that precise embodiment, and that various changes and modifications may be affected therein by one skilled in the art without departing from the scope or the spirit of the invention as defined in the following claims.

I claim:

1. A cutting instrument for human nasal surgery consisting of:
   an elongated portion extending along a first direction and having a first end means which is to be placed into a nostril during nasal surgery:
   a single cutting extension extending from one side of said elongated portion in a second direction from said elongated portion at approximately ninety degrees from said first direction which has first and second cutting edges which point in opposite directions parallel to said first direction and which extend in said second direction and which extension has a blunted non cutting end which extends beyond said cutting edges away from said elongated portion in said second direction.

2. A cutting instrument according to claim 1 in which said elongated portion is a stem designed for attachment to a handle.

3. A cutting instrument according to claim 1 in which said cutting extension is less than three and one-half millimeters in width along said first direction.

4. A cutting instrument according to claim 1 in which each of said first and second cutting edges extend in said second direction between two and six millimeters.

5. A cutting instrument according to claim 1 in which said cutting extension is placed approximately at said first end of said elongated portion.

* * * * *